United States Patent [19]

Sugiura

[11] Patent Number: 5,413,101
[45] Date of Patent: May 9, 1995

[54] PULSE OXIMETER PROBE

[75] Inventor: Keiichi Sugiura, Tokyo, Japan

[73] Assignee: Nihon Kohden Corporation, Tokyo, Japan

[21] Appl. No.: 212,924

[22] Filed: Mar. 15, 1994

[30] Foreign Application Priority Data

Mar. 15, 1993 [JP] Japan ............... 5-011119 to U

[51] Int. Cl.6 ............................................. A61B 5/00
[52] U.S. Cl. .................................. 128/633; 128/666; 356/41
[58] Field of Search ................... 128/633, 664–666; 356/41

[56] References Cited

U.S. PATENT DOCUMENTS 2,640,389  6/1953  Liston .............................. 128/633
4,334,544  6/1982  Hill et al. ........................... 128/686
5,247,931  9/1993  Morwood .......................... 128/633
5,279,295  1/1994  Martens et al. .................... 128/666

Primary Examiner—Lee S. Cohen
Assistant Examiner—Robert L. Nasser, Jr.
Attorney, Agent, or Firm—Sughrue, Mion, Zinn, Macpeak & Seas

[57] ABSTRACT

A pulse oximeter probe can be attached securely to the ear of a subject without compressing the site of measurement, and permits precise measurements and which can be used as a disposable product. A covering member formed as a tubular bag of a flexible synthetic resin is provided with light-emitting element and light-receiving element at opposite ends, and holding member consisting of main body and moving flap is inserted into the covering member.

6 Claims, 2 Drawing Sheets 5,413,101

PULSE OXIMETER PROBE

BACKGROUND OF THE INVENTION

1. Field of the Invention

This invention relates to a pulse oximeter probe that detects the pulsation or throbbing of blood flowing through a blood vessel in the living tissue so as to measure the oxygen saturation of blood and other blood-related parameters. The invention relates particularly to a pulse oximeter probe of a type that is to be attached to the ear of a subject.

2. Related Art

Conventional pulse oximeter probes which are to be used for measuring the oxygen saturation of blood and other blood-related parameters in the living tissue are available in two types depending on the mechanism for detecting the pulsation of blood flowing through blood vessels, i.e., by light transmission through the probe that is attached to a subject's finger, leg or earlobe or by light reflection from the probe that is attached to the forehead of the subject having a comparatively large amount of blood circulation.

A problem with the type of probe that is to be attached to a subject's finger or leg is that the subject is no longer free to use both hands or finds difficulty in walking. Furthermore, it is difficult for the analyst to acquire consistent data. On the other hand, less inconvenience will be caused to the life of the subject if the probe is attached to his earlobe.

A conventional pulse oximeter probe of the type that is to be attached to the earlobe is typically in the form of a clip. As shown in FIGS. 8 and 9, the probe comprises generally a pair of holding members 21 and 22 that are connected together at an end in such a way that they can pivot on a shaft 23. The holding members 21 and 22 are furnished with a light-emitting device 24 and a light-receiving device 25, respectively, in such a way that they are in a face-to-face relationship. The shaft 23 is fitted with a leaf spring (not shown) that urges the devices 24 and 25 to pivot in a direction in which they approach each other. The probe generally indicated at 27 can be attached to the earlobe 26 of a subject by holding it with the holding members 21 and 22.

However, the conventional oximeter probe of the clip type which is constructed in the manner just described above has three major drawbacks. First, the holding members 21 and 22 have to compress the earlobe 26 so as to detect the pulsation of blood flowing in the compressed area but, then, the quantity of blood circulation decreases to lower the precision of measurement. Second, the probe 27 which is attached to the earlobe 26 is liable to movements and, hence, errors due to the movement of the earlobe are most likely to occur if measurements are done while the subject is walking. Thirdly, the probe is fairly complex in construction and it is too expensive to be used as a disposable product.

The present invention has been accomplished under the circumstances and has as an object providing a disposable pulse oximeter probe that can be attached to the ear of a subject without compressing the site of measurement, that is less sensitive to unwanted movements of an object part such as the neck and which hence is capable of precise measurements.

SUMMARY OF THE INVENTION

This object of the present invention can be attained by a pulse oximeter probe of the type that detects the pulsation of blood in a blood vessel by reception of light at a light-receiving element after it is transmitted through a part of the living tissue following its emission from a light-emitting element, the pulse oximeter probe comprising: a covering member formed of a flexible material; the light-emitting element provided in either the opening in the end face at one end of said covering member or the opening in the lateral face at the other end of said covering member; the light-receiving element provided in either the opening in said lateral face or the opening in said end face; a holding member that is inserted into said covering member and which consists of a main body having a bent portion at one end and a moving flap connected pivotally to the other end of said main body; and an urging member that urges said moving flap in such a direction that it is parallel to said main body.

With the structural layout just described above, the bent portion of the main body of the holding member as it is inserted into the covering member is provided on the back face of either the light-emitting element or the light-receiving element whereas the distal end of the moving flap is provided on the back face of either the light-receiving element or the light-emitting element. As a result, the light-emitting and light-receiving elements come in a face-to-face relationship when the moving flap is brought to a position substantially parallel to the main body. Thus, by holding the earlobe of a subject securely between the main body and the moving flap so that the area around the entrance to the auditory meatus which abounds with elastic tissues is held between the light-emitting and light-receiving elements, excessive movements of the probe can be prevented without compressing blood vessels at the site of measurement, thereby insuring the pulsation of blood flow in blood vessels to be detected with high precision.

BRIEF DESCRIPTION OF THE PREFERRED EMBODIMENTS

DETAILED DESCRIPTION OF THE PREFERRED EMBODIMENTS

An example of the pulse oximeter probe of the present invention is described below with reference to accompanying drawings.

Figure 1:
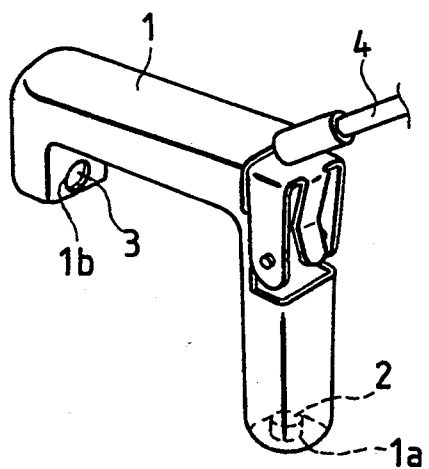
FIG. 1 is a perspective view showing the external appearance of an example of the pulse oximeter probe of the present invention.
Figure 2:
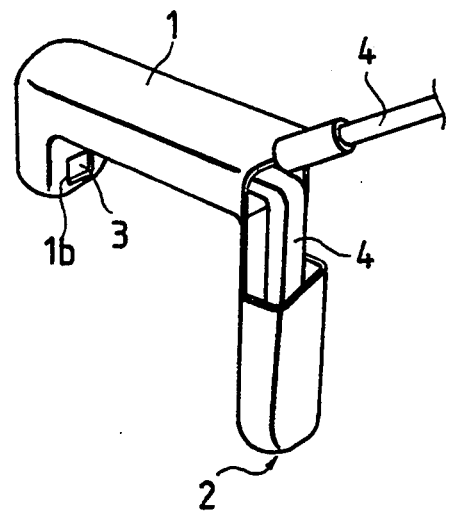
FIG. 2 is a perspective view showing the external appearance of the covering member in FIG. 1.
Figure 3:
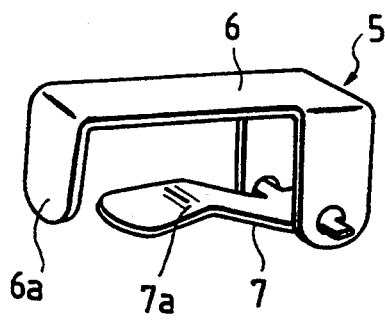
FIG. 3 is an illustration of the structure of a holding member which is one component of the probe shown in FIG. 1.
Figure 4:
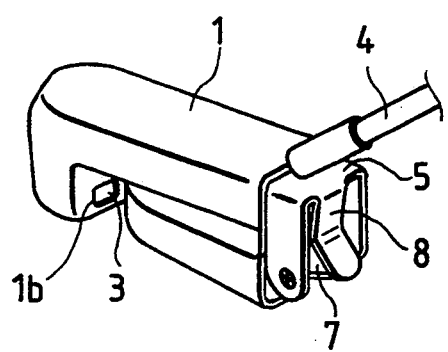
FIG. 4 is a perspective view showing the external appearance of the probe shown in FIG. 1, with the moving flap closed.
Figure 5:
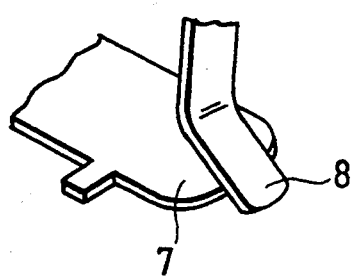
FIG. 5 is a perspective view showing the structure of the holding member in FIG. 4.
Figure 8:
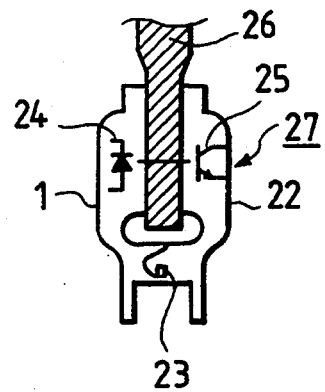
FIG. 8 is a side view showing the construction of a prior art pulse oximeter probe in a clip form.

FIGS. 1 to 6 show an example of the present invention. Reference is first made to FIGS. 1 and 2; a covering member 1 formed as a tubular bag of a synthetic resin such as Goretex has an opening 1a in the end face at one end, and a light-emitting element 2 is fitted in the opening 1a. Another opening 1b is provided in the lateral face at the other end of the covering member 1, and a light-receiving element 3 is fitted in the opening 1b. The light-emitting element 2 and the light-receiving element 3 are connected to an external measuring circuit via a lead wire 4. A holding member 5 (see FIG. 3) which is formed of a metal or a rigid synthetic resin is inserted into the covering member 1. The holding member 5 is composed of a main body 6 having a perpendicularly bent portion 6a at one end and a moving flap 7 connected pivotally to the other end of the main body 6. As shown in FIGS. 4 and 5, the moving flap 7 is so adapted that it can be held in a position substantially parallel to the main body 6 by means of an urging member 8 such as a leaf spring. When the holding member 5 is inserted into the covering member 1, the bent portion 6a will be positioned on the back face of the light-receiving element 3 whereas the distal end of the moving flap 7 will be positioned on the back face of the light-emitting element 2.

Figure 6:
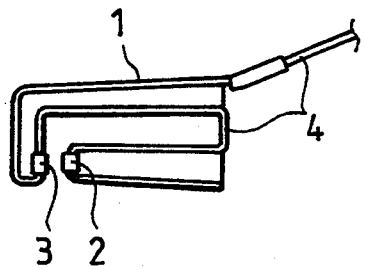
FIG. 6 is an illustration of the wire harnessing in the example shown FIG. 1.
Figure 9:
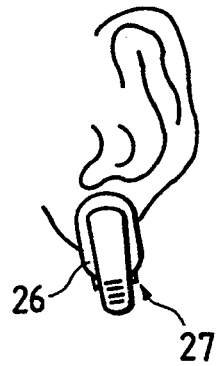
FIG. 9 is an illustration of the probe of FIG. 8 as it is attached to the earlobe of a subject.

The moving flap 7 has a raised portion 7a that bulges toward the main body 6 (see FIG. 3) and the earlobe of a subject can be fixed compressively between the main body 6 and the raised position 7a. As shown in FIG. 6, the lead wire 4 runs along the inner surfaces of the covering member 1.

Figure 7:
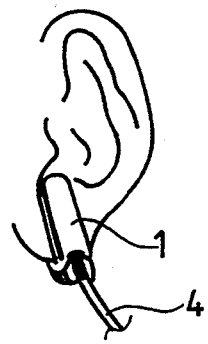
FIG. 7 is an illustration of the probe of FIG. 1 as it is attached to the earlobe of a subject.

In the example under consideration, the moving flap 7 shown in FIG. 3 is first opened and the earlobe of a subject is inserted between the moving flap 7 and the main body 6 as shown in FIG. 7; then, the moving flap 7 is closed, whereby the probe can be securely fixed to the subject's ear so that it will not move greatly even if the subject makes movement as in walking. In addition, the site of measurement between the light-emitting element 2 and the light-receiving element 3 is separate from the site where the probe is fixed and, hence, the pulsation of blood can be detected without compressing blood vessels in the site of measurement. Hence, the oxygen saturation of blood, pulse wave, pulse rate, blood pressure and other blood-related parameters can be measured with high precision. It should also be noted that the surface of the probe is formed of a flexible material such as Goretex and, hence, there is no possibility for the occurrence of rash and other skin disorders in the area where the probe is attached. That is worth particular mention is that the probe is disposable since its components can be formed at low cost.

The relative positions in which the light-emitting element 2 and the light-receiving element 3 are installed with respect to end portions of the covering member 1 may be reversed from the case shown in the example under consideration.

As described on the foregoing pages, the pulse oximeter probe of the present invention has the advantage that it can be held securely to the ear of a subject by means of the holding member that is inserted into the covering member. Further, the site of measurement will not be compressed by the light-emitting and light-receiving elements and, hence, unwanted movements of the probe due to movements of the object can be reduced while the pulsation of blood is detected with high precision.

What is claimed is:

1. A pulse oximeter probe comprising:
   a flexible covering member formed of a flexible material;
   a light-emitting element, for emitting a light to a living tissue, provided in one of an opening in an end face at one end of said covering member and an opening in a lateral face at the other end of said covering member;
   a light-receiving element for receiving the emitted light having passed through the living tissue to detect a pulsation of blood in a blood vessel, the light-receiving element being provided in the other opening;
   a holding member for holding the covering member in a predetermined portion of the living tissue, said holding member being inserted into and covered by said covering member; and
   an urging means for urging the holding member in a predetermined direction.

2. A pulse oximeter probe as claimed in claim 1, wherein the holding member comprises a main body having a bent portion at one end and a moving flap connected pivotally to the other end of said main body.

3. A pulse oximeter probe as claimed in claim 2, wherein the predetermined direction corresponds to a direction in such a manner that the moving flap is parallel to said main body.

4. A pulse oximeter probe as claimed in claim 2, wherein said moving flap includes a raised portion that bulges towards said main body, the predetermined portion being fixed between said main body and said raised portion, said raised portion being remote from a portion of said holding member that corresponds to the light-emitting member and the light-receiving member.

5. A pulse oximeter probe as claimed in claim 2, wherein the bent portion is positioned on a back face of one of the light emitting element and the light-receiving element and an end portion of the moving flap is positioned on a back face of the other element.

6. A pulse oximeter probe as claimed in claim 1, wherein the covering member is formed in a tubular shape.

* * * * *